US011103692B2

(12) United States Patent
Cakmak

(10) Patent No.: US 11,103,692 B2
(45) Date of Patent: Aug. 31, 2021

(54) ELECTRO-STIMULATION DEVICE FOR INNERVATION OF THE EXTERNAL EAR CANAL

(71) Applicant: Yusuf Ozgur Cakmak, Istanbul (TR)

(72) Inventor: Yusuf Ozgur Cakmak, Istanbul (TR)

( * ) Notice: Subject to any disclaimer, the term of this patent is extended or adjusted under 35 U.S.C. 154(b) by 163 days.

(21) Appl. No.: 16/308,578

(22) PCT Filed: Jun. 10, 2016

(86) PCT No.: PCT/TR2016/050176
§ 371 (c)(1),
(2) Date: Dec. 10, 2018

(87) PCT Pub. No.: WO2017/213601
PCT Pub. Date: Dec. 14, 2017

(65) Prior Publication Data
US 2019/0151646 A1    May 23, 2019

(51) Int. Cl.
*A61N 1/04*    (2006.01)
*A61H 39/00*    (2006.01)
(Continued)

(52) U.S. Cl.
CPC .......... *A61N 1/0456* (2013.01); *A61B 5/4836* (2013.01); *A61B 5/6817* (2013.01);
(Continued)

(58) Field of Classification Search
USPC .......................................................... 607/149
See application file for complete search history.

(56) References Cited

U.S. PATENT DOCUMENTS 9,089,691 B2    7/2015  Libbus et al.
2003/0195588 A1*  10/2003  Fischell .................. A61N 2/02
                                                          607/55
(Continued)

FOREIGN PATENT DOCUMENTS

DE    10 2005 003 735 A1    7/2006
DE    10 2010 015 278 A    10/2011

OTHER PUBLICATIONS

International Search Report (ISR) for International Application No. PCT/TR2016/050176 dated Feb. 6, 2017.
(Continued)

*Primary Examiner* — Nicole F Lavert
*Assistant Examiner* — Nicole F Johnson
(74) *Attorney, Agent, or Firm* — Ladas & Parry LLP

(57) ABSTRACT

An electro-stimulation device where the innervation of the external ear canal is transcutaneously stimulated for treatment of neurological diseases. More particularly, an electrostimulation device having a cylindrical ear insert the surface of which contains at least one electrode being provided with a stimulation end adapted to be transcutaneously attached to the innervation of the external ear canal of a human. The electro-stimulation device is configured to stimulate anterior, superior, posterior or inferior positions of the external ear canal to stimulate simultaneously, sequentially or separately the trigeminal nerve, facial nerve, vagus nerve or glossopharyngeal nerve of the external ear canal. A control unit and a wireless communication unit are preferably placed in the cylindrical ear insert and the control unit is configured adjust the stimulation based on sensor signals such as motion sensor (accelerometer), video/image sensor (blinking movements), EEG, ECG, voice/swallowing sensor, temperature sensor.

31 Claims, 2 Drawing Sheets

Figure 1:
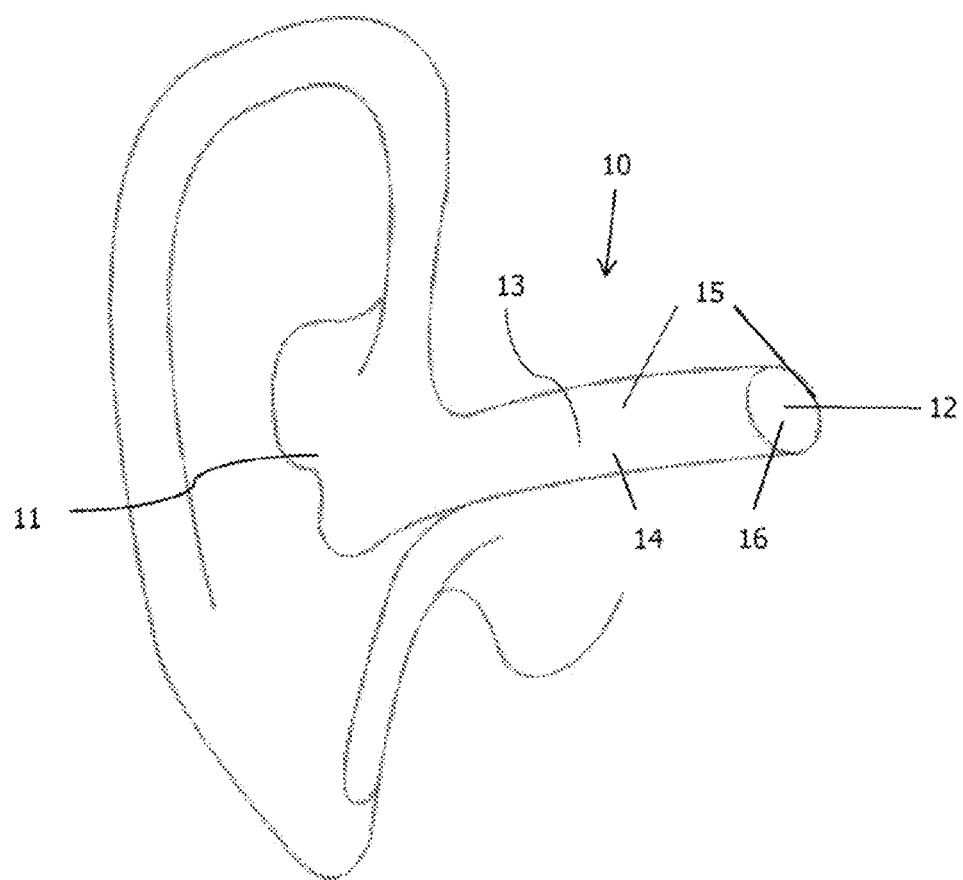

(51) Int. Cl.
*A61B 5/00* (2006.01)
*A61N 1/36* (2006.01)
*A61N 1/05* (2006.01)
*A61B 5/11* (2006.01)

(52) U.S. Cl.
CPC ......... *A61H 39/002* (2013.01); *A61N 1/0476* (2013.01); *A61N 1/36014* (2013.01); *A61N 1/36036* (2017.08); *A61B 5/11* (2013.01); A61H 2201/5007 (2013.01); A61H 2201/5084 (2013.01); A61H 2205/027 (2013.01); A61H 2230/00 (2013.01); A61N 1/0526 (2013.01); A61N 1/36021 (2013.01); A61N 1/36053 (2013.01); A61N 1/36067 (2013.01)

(56) References Cited

U.S. PATENT DOCUMENTS

| | | | |
|---|---|---|---|
| 2009/0287035 A1 | 11/2009 | Dietrich et al. | |
| 2010/0198282 A1* | 8/2010 | Rogers ................ | A61F 7/00 607/3 |
| 2015/0360030 A1 | 12/2015 | Cartledge et al. | |

OTHER PUBLICATIONS

Written Opinion (WO) for International Application No. PCT/TR2016/050176 dated Feb. 6, 2017.

* cited by examiner

ELECTRO-STIMULATION DEVICE FOR INNERVATION OF THE EXTERNAL EAR CANAL

RELATED APPLICATION

This application is a national phase entry under 35 USC 371 of International Patent Application No.: PCP/TR2016/050176 filed on 10 Jun. 2016, the disclosure of which is incorporated in his entirety by reference herein.

TECHNICAL FIELD OF THE PRESENT INVENTION

The present invention relates to an electro-stimulation device where the innervation of the external ear canal is transcutaneously stimulated for treatment of neurological diseases.

BACKGROUND OF THE PRESENT INVENTION

Abnormal resting over-activity such as tremors can be caused by various conditions or medicaments that affect the nervous system, including Parkinson's disease (PD), liver failure, alcoholism, mercury or arsenic poisoning, lithium, and certain antidepressants. Rigidity, bradykinesia and postural instability are the other main motor symptoms of the Parkinson's disease besides tremors. Parkinson's disease is a progressive movement disorder of the central nervous system, meaning that symptoms continue and worsen over time. It is caused by the degeneration of dopaminergic neurons in the substantia nigra of the basal ganglia in the midbrain. According to European Parkinson's Disease Association, it is estimated that 6.3 million people in the world are living with Parkinson's disease. The cause is unknown, and although there is presently no cure, there are treatment options such as medication and surgery to manage its symptoms. Stimulation of different parts of the brain with different techniques can be successfully used for the treatment of Parkinson's disease.

The main objectives of the deep brain stimulation (DBS) devices are stimulation of the subthalamic nucleus and as a consequence, activation of the supplementary motor areas and premotor areas and normalization of the abnormal resting over-activity in the motor system.

Subthalamic Nucleus-Deep Brain Stimulation (STN-DBS) is an invasive but effective approach to Parkinson's disease (PD) symptoms. Standard STN-DBS for PD is usually delivered 100 to 250 Hz (130 Hz-185 Hz) with a voltage level of 1-4V and pulse width of 60 microseconds. On the other hand, to achieve specific effects, different frequencies are generally used; for instance while in order for improving swallowing, freezing and axial gait functions 60 Hz is considered effective, 130 Hz is not effective. Moreover, for verbal fluency 60 Hz works better than 130 Hz. On the basis of the available data, it is to be noted that a particular stimulation frequency may be needed for alleviating different symptoms of PD. For the tremor resistant patients, the frequency is generally selected as 180 Hz.

Current applications to stimulate the subthalamic nucleus include intracranial electrode placement, which is called deep brain stimulation. The process of deep brain stimulation of the subthalamic nucleus requires neurosurgery, which is an extremely invasive intervention for the Parkinson's patient. In this neurosurgical operation, electrodes are placed into the subthalamic nucleus region which includes a map of muscles of the human body. The neurons in this muscle map have feedbacks (like stretch, length etc.) from muscles of the human body. In other words to stimulate the STN externally, a nerve which is related with muscle innervation should be stimulated.

The frequency and the intensity of these stimulators can be altered wirelessly with an external unit. The United States patent application U.S. Pat. No. 5,707,396 discloses a method of arresting degeneration of the substantia nigra by high frequency stimulation of subthalamic nucleus. This method needs the electrodes to be neurosurgically implanted into substantia nigra besides surgical implantation of the battery. However, surgical device applications are likely to have side effects. Moreover, the battery of the stimulator is placed under the thorax skin while the electrodes inserted into the brain tissue and the wires go under the skin, making this a very invasive procedure.

To address this problem and to improve the quality of life of patients, transcutaneous stimulation of the cranial nerves can also be used for treatment of neurological disorders. The ear is host to branches of cranial nerves, including, vagus (cranial nerve X), trigeminal (cranial nerve V), facial (cranial nerve VII) and glossopharyngeal (cranial nerve IX) nerves, stimulation of which is helpful in treating symptoms of vestibular and neurological disorders, such as Parkinson's disease. To take advantage of this, external devices placed on or in the ear can be used to stimulate these nerves.

An example of such a device may be referred to as U.S. Pat. No. 5,514,175, which discloses a treatment device described as a low voltage, multipoint auricular stimulator for dysfunctions in neural pathways by acting upon multiple auricular points.

Another example may be referred to as US 2003/0195588, which discloses a device to be situated in a patient's ear canal, which can provide electrical or caloric stimulation to innervation of the external ear canal.

A further example may be referred to as U.S. Pat. No. 9,089,691, which discloses a device to stimulate the vagus nerve by electrodes placed inside the patient's external ear canal.

The present invention aims to provide an electro-stimulation device that targets the auricular branches of all four cranial nerves critical to treatment of symptoms of PD, namely, vagus, trigeminal, facial and glossopharyngeal nerves together in order to present an effective and noninvasive treatment method. The device, including its control unit and power source, is fully insertable in the patients external ear canal, therefore providing treatment in an unnoticeable way and permitting the patients to go on with their daily activities without discomfort.

The present invention provides an electro-stimulation device as provided by the characterizing features defined in claim 1.

OBJECTS OF THE PRESENT INVENTION

The object of the invention is to provide an electro-stimulation device where the vagus, trigeminal, facial and glossopharyngeal nerves are stimulated transcutaneously by which treatment of neurological diseases such as Parkinson disease, Migraine, movement disorders, depression or pain management can be achieved.

Another object of the invention is to provide an electro-stimulation device where the vagus, trigeminal, facial and glossopharyngeal nerves are stimulated via their respective auricular branches surrounding the external ear canal.

Another object of the invention is to provide an electro-stimulation device where the stimulation parameters of the vagus, trigeminal, facial and glossopharyngeal nerves are changed according to the data collected by a plurality of peripheral sensing units.

BRIEF DESCRIPTION OF THE TECHNICAL DRAWINGS

Accompanying drawings are given solely for the purpose of exemplifying an electro-stimulation device, whose advantages over prior art were outlined above and will be explained in brief hereinafter.

The drawings are not meant to delimit the scope of protection as identified in the Claims, nor should they be referred to alone in an effort to interpret the scope identified in said Claims without recourse to the technical disclosure in the description of the present invention.

FIG. 1 demonstrates a schematic frontal view of the sensory innervation of the external ear canal.

Figure 2:
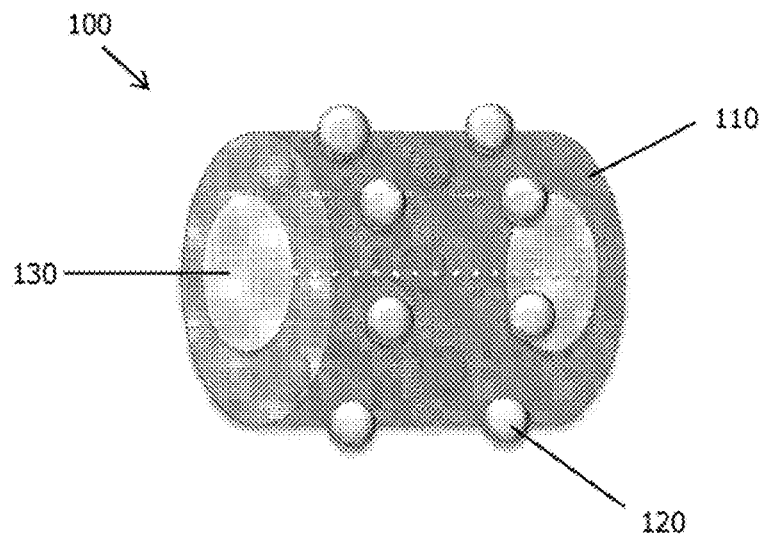

FIG. 2 demonstrates a perspective view of the electro-stimulation device.

Figure 3:
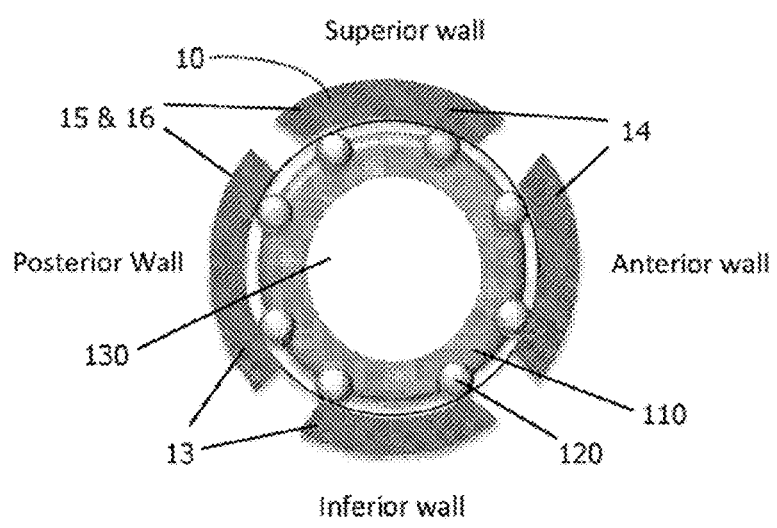

FIG. 3 demonstrates a side view of the electrostimulation device inside the external ear canal.

DETAILED DESCRIPTION OF THE PRESENT INVENTION

The following numerals are referred to in the detailed description of the present invention:
10 External ear canal
11 Auricle
12 Tympanic membrane
13 Vagus nerve
14 Trigeminal nerve
15 Facial nerve
16 Glossopharyngeal nerve
100 Electro-stimulation device
110 Ear insert
120 Electrode
130 Acoustic channel The present invention discloses an electro-stimulation device (100) connected to at least one sensor, having at least one electrode (120) and a stimulation end of which controlling the stimulation process based on the collected data, also through said electro-stimulation device (100) as will be delineated hereinafter.

The electro-stimulation device (100) of the invention provides that fine-tuning of parameters such as current, voltage, polarization, signal form is carried out. The at least one electrode (120) of the electro-stimulation device (100) is adapted to be transcutaneously attached to the innervation of the external ear canal, namely the vagus, trigeminal, facial or glossopharyngeal nerves.

The innervation of the external ear canal (10) has a well-defined structure that is well known in the art. The nerve supply of the external ear canal is provided mainly by the auricular branch of the vagus nerve (13) on the inferior and posterior canal walls and the auriculotemporal nerve (a branch of the mandibular division of the trigeminal nerve (14)) on the anterior and superior canal walls. In addition, a sensory branch of the facial nerve (15) contributes to the innervation of the postero-superior canal wall and a branch of the glossopharyngeal nerve (16) contributes to the innervation of the external ear canal proximal to the tympanic membrane and at the postero-superior canal wall (Alvord et al., 1997, J. Am. Acad. Audiol. 8, p. 383-390).

Because there are many nerves that go to the ear that also innervate other part of the head or neck, it is possible that ear pain may have its origin in another part of the head or neck (referred otalgia). For the same reason, stimulation of the innervation of the ear may have an effect on symptoms in other parts of the head and neck. For example, dry mouth (xerostomia) is a frequent (>60%) symptom of Parkinson's disease (Cersosimo et al., 2011, J Parkinsons Dis. 1, p. 169-173). This symptom may be treated by stimulation of facial (15), trigeminal (14) and glossopharyngeal (16) nerves, which innervate both the ear and the salivary glands.

Dysphagia (difficulty or discomfort in swallowing) is also a common symptom of Parkinson's disease. Aspiration pneumonia, malnutrition and dehydration are some of the complications that can arise due to this disorder (Tjaden, 2008, Top Geriatr Rehabil 24, p. 115-126). There are many nerves involved with the act of swallowing. Among these nerves are the facial nerve (15) (oral commissure control and bolus manipulation within the oral cavity during mastication), the glossopharyngeal nerve (16) (reflexive portion of pharyngeal swallow and control of the motion of the constrictor muscles utilized in bolus propulsion and clearance) and the vagus nerve (13) (vocal cord adduction during the bolus passage and allowing appropriate glottic closure during the cough reflex initiation of swallow) (McCulloch et al., 2006, *Head and neck disorders affecting swallowing*, GI Motility Online). Transcutaneous stimulation of these nerves from the external ear canal may alleviate some of these symptoms.

Similarly, damage to the vagus nerve (13), for example after a viral infection, can be the cause of refractory chronic cough (sensory neuropathic cough) as the vagus nerve also innervates the larynx and is responsible for the cough reflex. Persistent dry cough related to ear wax buildup in the external ear canal is referred to as Arnold ear-cough reflex. (Ryan et al., 2014, J Thorac. Dis. 6 (Suppl. 7), p. 748-752) Consequently, chronic cough caused by damage to the vagus nerve elsewhere in the head and neck may be treated by transcutaneous stimulation of the vagus nerve (13).

In addition, dysautonomia (dysfunction of the autonomic nervous system) is also one of the symptoms of Parkinson's disease affecting 70% to 80% of patients. (Zesiewicz et al., 2003, Curr Treat Options Neurol. 5, p, 149-160) It is possible to treat these symptoms by transcutaneous stimulation of the sympathetic nerves innervating the arteries of the external ear canal (10), posterior auricular artery, superficial temporal artery and deep auricular artery. Therefore, it is possible to effectuate modulation of sympathetic system fibers on the deep auricular artery, superficial temporal artery and deep auricular artery to alleviate Autonomic dysfunction in Parkinson's disease.

According to a first embodiment, electro-stimulation device (100) comprises a cylindrical ear insert (110), the lateral surface of which contains at least one electrode (120), Preferably, electro-stimulation device (100) comprises at least four pairs of electrodes (120) placed on the surface of the ear insert (110) in such a way that the position of at least two electrodes (120) correspond to the anterior, superior, posterior and inferior positions respectively. Electrodes (120) corresponding to the aforementioned positions may be activated simultaneously, alternatively or in a synchronized manner, depending on which of the nerves are desired to be stimulated.

In this way, a three dimensional irregular electron cloud capable of covering the length of the external ear canal (10) is generated by the electrodes. Said three dimensional irregular electron cloud can be dynamically moved along the external ear canal (10) and its shape can be modified depending on the manner of activation of electrodes (120).

The placement of said electrodes (120) on said ear insert (110) is determined by the innervation map of the external ear canal. The arrangement of electrodes (120) allows the vagus 13, trigeminal 14, facial 15 and glossopharyngeal 16 nerves to be stimulated simultaneously, sequentially or separately. To ensure the stimulation of the glossopharyngeal nerve 16, electro-stimulation device (100) is placed in the bony part of the external ear canal, proximal to the tympanic membrane.

In the operational position, the laterally placed electrodes (120) lean on the inner surface of the skin in the patient's external ear canal 10 at predetermined points chosen to enable the stimulation of vagus 13, trigeminal 14, facial 15 and glossopharyngeal 16 nerves based on the innervation map of the external ear canal.

In one embodiment of the invention, a control unit is placed in the body of said cylindrical ear insert (110). In yet another embodiment of the invention, a communication unit placed in the body of said cylindrical ear insert (110) is in wireless communication with an external control unit and provides a certain parameter signal as voltage or current signal and preferable in the form of current-amplified signal to said at least one electrode (120). Said control unit may operate in an open loop or a dosed loop system. In the open loop system, the voltage and frequency of the stimulation signal is determined by user-entered parameters. In the closed loop system, the voltage and frequency of the stimulation signal is determined by the feedback from physiological sensors, such as an accelerometer or a video capturing peripheral that collects blinking data or EEG or ECG etc.

Said ear insert (110) may be an elastomeric ear insert made out of polymeric foam or other materials that are used in the manufacture of ear plugs. Alternatively said ear insert (110) may be a stent. In this way, the ear insert (110) takes the shape of the external ear canal of the patient and ensures that the device is not displaced and the operational position of the electrode (120) in the ear canal is maintained.

In one embodiment of the invention, an acoustic channel (130) runs through the length of the ear insert to allow sound from the outside to reach the tympanic membrane.

In a variant embodiment of the invention, acoustic channel (130) is replaced by an amplifier to amplify sound from the outside as it reaches the tympanic membrane. In this way electro-stimulation device (100) can also be used as a hearing aid.

In a variation of the invention, electro-stimulation device (100) may comprise a system that selectively varies specific operational parameters according to different symptoms in the same session. Generally, while the frequency signal set at 60 Hz cures the voice-related parameters (basically voice quality) of a patient, 130 Hz cures the rigidity and postural instability. Therefore, according to the present invention, data collected from a plurality of sensors such as for instance an inertial measurement unit being embodied in peripheral sensing units in signal communication with the control unit of the present electro-stimulation device (100), can be used in selectively applying varying treatment parameters. Likewise, the intensity, speed and for instance swallowing duration etc. of a patient can be analyzed by a speech processing software (preferably real-time or as a pre-treatment recorded sample) and the data collected as such can thereby be used in selectively applying varying treatment parameters as explained above. Different treatment routines with varying frequencies can be subsequently applied in the manner that while a frequency value is adopted for a predetermined time duration, the frequency can be subsequently varied for another predetermined time duration in a symptom-specific manner.

In one embodiment of the invention, electro-stimulation device (100) comprises at least one communication unit, which enables realizing of communication with other devices. Typically, the control unit enables signals to be sent to/received from electrodes (120), controlling the driving circuit, receiving signals from the stimulating end and controlling the communication unit.

A video capturing peripheral can enable receiving of images from the patient and hence enabling visual monitoring of symptoms such as tremors. The received images are then processed by known image processing techniques and information such as intensity of tremors is acquired.

Alternatively, an inertial measurement unit as a peripheral unit with an accelerometer can be placed in the body of the ear insert (110), the activity of which is to be periodically monitored. Therefore, the intensity of disturbances can be sensed by measuring the acceleration of the body and filtering out signals coming from the head and the neck. Upon measurement of the disturbance level, the stimulation signal can be adjusted to target the specific needs of a patient, i.e. so as to be adapted to the changing state of the patient.

The adjustments to the stimulation signal can typically be carried out by changing the amplitude, frequency, pulse width, and pulse shape such as the harmonic content of the periodic pulses etc. The phases of the electro-stimulating devices relative to each other can be adjusted if a multitude of electro-stimulating devices are used.

Electra-stimulation device (100) typically comprises a communication unit in signal communication with the electronic control module, enabling communication with other devices such as remote control units, computers, peripheral measurement/sensor units etc. The communication unit conventionally supports known communication protocols/standards (IR, USB, IEEE 802 family, Bluetooth, RF communication interface, RS-232, RS-422, RS-485, SPI (serial peripheral interface) i2c, as well as proprietary interfaces and/or protocols etc.).

The driving circuit typically enables increased driving power levels. Therefore, power can be fed to the electrodes (120) by the driving circuit.

In the preferred embodiment of the invention, different stimulating signal parameters (voltage, current, signal period, polarization and signal form) can be adjusted and the signal produced by the control unit may have a voltage of 0V-15V and the frequency of 2 Hz-250 Hz. The parameters of the stimulating signal can be automatically changed by the control unit depending on the situation of the patient or they can be remotely changed via a remote unit by an authorized user such as a physician, upon evaluating the situation of the patient. The frequency of the stimulation signals being generated is preferably between 2-250 Hz. It is worthy of note that lower limit of said frequency is selected as 2 Hz because 2 Hz is found to be a frequency value that induces peripheral nerve regeneration by protecting and regenerating the biological stimulation pathway, the axons elongated from the intrinsic auricular muscles to the muscle coordination related brain structures.

According to one embodiment of the present invention, the elastomeric ear insert (110) can be configured in the form of an expandable stent to be placed in the external ear canal (10).

In a variation of the invention, two electro-stimulation devices (100) or ear-insertable devices are simultaneously operated for both ears of a patient in synchronized manner as the present inventors have found that stimulation of cranial nerves at both sides in a synchronized manner synergistically induce positive results associated with the treatment.

In a further variation of the invention, electro-stimulation device (100) also monitors frequency and wavelength of the applied voltage or current electrical signal through the driving circuit, which is advantageous in that the driving circuit in electrical connection with a feedback loop ensures that no variations occur in the stimulation signal during the stimulating states of subsequent periods of the stimulation signal.

In a further variation of the invention, the control unit is preferably integral with electro-stimulation device (100) and can be controlled by a remote terminal through an appropriate software module to adjust parameters of the stimulation procedure.

In a further variation of the invention, the stimulation signal can include signal components in the bursting frequencies. As is known to the skilled worker, bursting is a phenomenon of neuron activation patterns where periods of rapid action potential spiking are followed by resting phase periods.

In one embodiment of the present invention, art electro-stimulation device (100) is proposed, comprising a generally tubular or substantially cylindrical ear insert (110) the surface of which contains at least one electrode (120) being provided with a stimulation end adapted to be transcutaneously attached to the innervation of the external ear canal (10) of a human.

In a further embodiment of the present invention, said electro-stimulation device (100) comprises at least one electrode (120) placed on the surface of the ear insert (110) with the stimulation end there of being adapted to generate an electrical stimulating signal during a stimulating state in the manner that the position of at least one electrode (120) corresponds to the anterior, superior, posterior or inferior positions of the external ear canal (10) in stimulating contact with trigeminal nerve (14), facial nerve (15) or glossopharyngeal nerve (16) of the external ear canal (10).

In a still further embodiment of the present invention, the position of at least one electrode (120) corresponds to the anterior, superior, posterior or inferior positions of the external ear canal (10) in stimulating contact with vagus nerve (13) of the external ear canal (10).

In a yet still further embodiment of the present invention, the ear insert (110) is elastomeric to provide a tight-fit surface relation with the external ear canal (10).

In a yet still further embodiment of the present invention, electro-stimulation device (100) comprises at least two electrodes (120) on different longitudinal orientations of said cylindrical ear insert (110).

In a yet still further embodiment of the present invention, electro-stimulation device (100) comprises at least two electrodes (120) on different radial orientations of said cylindrical ear insert (110).

In a yet still further embodiment of the present invention, electro-stimulation device (100) comprises four pairs of electrodes (120) placed on the surface of the ear insert (110) in such a way that the position of at least two electrodes (120) correspond to the anterior, superior, posterior and inferior positions respectively.

In a yet still further embodiment of the present invention, electro-stimulation device (100) comprises at least four electrodes (120) in stimulating contact with vagus nerve (13), trigeminal nerve (14), facial nerve (15) and glossopharyngeal nerve (16) of the external ear canal (10).

In a yet still further embodiment of the present invention, vagus nerve (13), trigeminal nerve (14), facial nerve (15) and glossopharyngeal nerve (16) of the external ear canal (10) are stimulated simultaneously, sequentially or separately.

In a yet still further embodiment of the present invention, electro-stimulation device (100) is placed in the bony part of the external ear canal (10) proximate the tympanic membrane.

In a yet still further embodiment of the present invention, laterally placed electrodes (120) of the cylindrical ear insert (110) lean on the inner surface of the skin of the external ear canal (10).

In a yet still further embodiment of the present invention, electro-stimulation device (100) comprises at least four electrodes (120) at predetermined points based on the innervation map of the external ear canal in stimulating contact with vagus nerve (13), trigeminal nerve (14), facial nerve (15) and glossopharyngeal nerve (16) of the external ear canal (10).

In a yet still further embodiment of the present invention, electro-stimulation device (100) comprises at least four electrodes (120) at predetermined points, three electrodes (120) of which being in stimulating contact with facial nerve (15), trigeminal nerve (14) and glossopharyngeal nerve (16) whereby xerostomia symptoms are targeted.

In a yet still further embodiment of the present invention, electro-stimulation device (100) comprises at least four electrodes (120) at predetermined points, three electrodes (120) of which being in stimulating contact with facial nerve (15), vagus nerve (13) and glossopharyngeal nerve (16), whereby dysphagia symptoms are targeted.

In a yet still further embodiment of the present invention, electro-stimulation device (100) comprises at least four electrodes (120) at predetermined points, one electrode (120) of which being in stimulating contact with vagus nerve (13), whereby chronic cough symptoms are targeted.

In a yet still further embodiment of the present invention, electro-stimulation device (100) comprises a control unit and a wireless communication unit placed within said cylindrical ear insert (110).

In a yet still further embodiment of the present invention, electro-stimulation device (100) provides a voltage or current signal and preferably in the form of current-amplified signal by said at least one electrode (120).

In a yet still further embodiment of the present invention, the control unit of electro-stimulation device (100) is configured to gradually change the electrical stimulating signal applied by the stimulation end in response to signals transmitted from a sensor unit.

In a yet still further embodiment of the present invention, said sensor unit is an accelerometer or a video capturing peripheral that collects blinking activity data or EEG or ECG.

In a yet still further embodiment of the present invention, said stimulation end is configured to be directly attached to the inner surface of the external ear canal (10) so as to establish a direct contact relation therewith.

In a yet still further embodiment of the present invention, said stimulation end is configured to transcutaneously stimulate the innervation of the external ear canal (10) from the bony part of the external ear canal (10).

In a yet still further embodiment of the present invention, said electrical stimulating signal parameters include sign, amplitude, frequency, signal period, signal form, harmonic content and pulse width of voltage and/or current.

In a yet still further embodiment of the present invention, said electrodes (120) are configured to be in the form of pad-shaped electrodes (120) attached to or embedded onto the lateral surface of the ear insert (110).

In a yet still further embodiment of the present invention, polarity of the stimulating signal is adjusted by applying positive and negative signals in consecutive periods.

In a yet still further embodiment of the present invention, operational position of the electrode (120) is maintained by the tight fit of the ear insert (110) into the patient's ear canal.

In a yet still further embodiment of the present invention, the control unit processes data collected by the video capturing peripheral such that natural blinking movements are differentiated from blinking movements induced by the stimulating signal whereby at least one threshold value of the stimulating signal is determined in view of the natural blinking movements being ignored.

In a yet still further embodiment of the present invention, values of electrical stimulating signal parameters are selectively varied according to data collected by at least one of sensing units including an inertial measurement unit, a voice recording unit or an image capturing unit.

In a yet still further embodiment of the present invention, the inertial measurement unit with an accelerometer in signal communication with the control unit is provided to collect movement data from a human body.

In a yet still further embodiment of the present invention, the accelerometer is placed in the body of the ear insert (110) and signals coming from head and neck are filtered out.

In a yet still further embodiment of the present invention, a voice recording unit in signal communication with the control unit is provided to monitor voice parameters including intensity, speed and swallowing duration of a patient.

In a yet still further embodiment of the present invention, voice parameters including intensity, speed and swallowing duration are analyzed real-time or as a pre-recorded sample.

In a yet still further embodiment of the present invention, an image capturing unit in signal communication with the control unit is provided to capture images from different body portions or extremities of a patient to detect symptoms such as tremors.

In a yet still further embodiment of the present invention, an acoustic channel (130) is open through the length of the ear insert to allow sound from the outside to reach the tympanic membrane.

In a yet still further embodiment of the present invention, the ear insert comprises an amplifier to amplify sound from the outside as it reaches the tympanic membrane In a yet still further embodiment of the present invention, the signal produced by the control unit has a voltage of 0V-15V and the frequency thereof is between 2 Hz-250 Hz.

In a yet still further embodiment of the present invention, the two electro-stimulation devices (100) are operable in a simultaneous manner in the manner that the electrical stimulating signal generated during a stimulating state is applied by said two electro-stimulation devices (100) at both ears in a synchronized manner.

In a yet still further embodiment of the present invention, electro-stimulation device (100) comprises a temperature sensor such that temperature of the stimulation end is continuously monitored to avoid excessive heating thereof beyond a predetermined limit.

In a yet still further embodiment of the present invention, electro-stimulation device (100) is operated such that the stimulation end's initial temperature and temperature thereof at the end of a predetermined inactive period prior to the stimulation are monitored and the active state temperature of the stimulation end is intermittently decreased to the temperature of a respective external ear canal region as measured at the end of the predetermined inactive period of the stimulation end.

In a yet still further embodiment of the present invention, the stimulating signal includes signal components in the bursting frequencies.

In a yet still further embodiment of the present invention, the intensity, speed and swallowing duration values are analyzed by a speech processing software.

In a yet still further embodiment of the present invention, frequency and wavelength of the applied electrical stimulating signal is continuously monitored through a driving circuit in electrical connection with a feedback loop to ensure that no variations occur in the stimulation signal during the stimulating states of subsequent periods of the stimulation signal.

In a yet still further embodiment of the present invention, the control unit is preferably integral with electro-stimulation device (100).

In a yet still further embodiment of the present invention, one of the electrodes (120) is used as the cathode electrode (120) and the cathode and anode electrodes (120) are on the same or different longitudinal or radial positions on the ear insert (110).

In a yet still further embodiment of the present invention, said electro stimulation device (100) comprises at least one electrode (120) placed on the surface of the ear insert (110) with the stimulation end thereof being adapted to generate an electrical stimulating signal during a stimulating state in the manner that the position of at least one electrode (120) is adapted to transcutaneously stimulate sympathetic nerves innervating posterior auricular artery, superficial temporal artery or deep auricular artery of the external ear canal (10).

The invention claimed is:

1. An electro-stimulation device (100) comprising a tubular ear insert (110), said insert having a surface which contains at least one electrode (120) provided with a stimulation end adapted to be transcutaneously attached to the innervation of the external ear canal (10) of a human characterized in that;
said electro-stimulation device (100) comprises at least four pairs of electrodes (120) configured to be placed on the surface of the ear insert (110) with the stimulation end thereof being adapted to generate an electrical stimulating signal during a stimulating state wherein at least two electrodes (120) correspond to each of anterior, superior, posterior or inferior positions of the external ear canal (10) respectively and are adapted to be place at predetermined points based on an innervation map of the external ear canal so as to be in stimulating contact with trigeminal nerve (14), facial nerve (15), glossopharyngeal nerve (16) or vagus nerve (13) of the external ear canal (10),
the tubular ear insert (110) is elastomeric to provide a tight-fit surface relation with the external ear canal (10),
at least two of said electrodes (120) are on different longitudinal or radial orientations of said cylindrical ear insert (110), and,
the electro-stimulation device (100) is configured to be placed in the bony part of the external ear canal (10) proximate the tympanic membrane said electrodes (120) are configured to stimulate vagus nerve (13), trigeminal nerve (14), facial nerve (15) and glossopharyngeal nerve (16) of the external ear carnal (10) simultaneously, sequentially or separately.

2. An electro-stimulation device (100) as set forth in claim 1, characterized in that laterally placed electrodes (120) of the cylindrical ear insert (110) are configured to lean on the inner surface of the skin of the external ear canal (10).

3. An electro-stimulation device (100) as set forth in claim 1, characterized in that electro-stimulation device (100) comprises at least four electrodes (120) at predetermined points, three electrodes (120) of which are configured to be in stimulating contact with facial nerve (15), trigeminal nerve (14) and glossopharyngeal nerve (16) whereby xerostomia symptoms are targeted.

4. An electro-stimulation device (100) as set forth in claim 1, characterized in that electro-stimulation device (100) comprises at least four electrodes (120) at predetermined points, three electrodes (120) of which are configured to be in stimulating contact with facial nerve (15), vagus nerve (13) and glossopharyngeal nerve (16), whereby dysphagia symptoms are targeted.

5. An electro-stimulation device (100) as set forth in claim 1, characterized in that electro-stimulation device (100) comprises at least four electrodes (120) at predetermined points, one electrode (120) of which is configured to be in stimulating contact with vagus nerve (13).

6. An electro-stimulation device (100) as set forth in claim 1, characterized in that electro-stimulation device (100) comprises a control unit and a wireless communication unit placed within said cylindrical ear insert (110).

7. An electro-stimulation device (100) as set forth in claim 1, characterized in that electro-stimulation device (100) provides a voltage or current signal-in form of current-amplified signal by said at least one electrode (120).

8. An electro-stimulation device (100) as set forth, in claim 6, characterized in that the control unit of said electro-stimulation device (100) is configured to gradually change the electrical stimulating signal applied by the stimulation end in response to signals transmitted from a sensor unit.

9. An electro-stimulation device (100) as set forth in claim 7, characterized in that said sensor unit is an accelerometer or a video capturing peripheral that collects blinking activity data or EEG or ECG.

10. An electro-stimulation device (100) as set forth in claim 1, characterized in that said stimulation end is configured to be directly attached to the inner surface of the external ear canal (10) so as to establish a direct contact relation therewith.

11. An electro-stimulation device (100) as set forth in claim 1, characterized in that said stimulation end is configured to transcutaneously stimulate the innervation of the external ear canal (10) from the bony part of the external ear canal (10).

12. An electro-stimulation device (100) as set forth in claim 7, characterized in that said electrical stimulating signal parameters include sign, amplitude, frequency, signal period, signal form, harmonic content and pulse width of voltage and/or current.

13. An electro-stimulation device (100) as set forth in claim 1, characterized in that said electrodes (120) are configured to be in the form of pad-shaped electrodes (120) attached to or embedded onto the lateral surface of the ear insert (110).

14. An electro-stimulation device (100) as set forth in claim 1, characterized in that polarity of the stimulating signal is adjusted by applying positive and negative signals in consecutive periods.

15. An electro-stimulation device (100) as set forth in claim 1, characterized in that operational position of the electrode (120) is configured to be maintained by the tight fit of the ear insert (110) into the patient's ear canal.

16. An electro-stimulation device (100) as set forth in claim 9, characterized in that the control unit processes data collected by the video capturing peripheral such that natural blinking movements are differentiated from blinking movements induced by the stimulating signal whereby at least one threshold value of the stimulating signal is determined in view of the natural blinking movements being ignored.

17. An electro-stimulation device (100) as set forth in claim 8, characterized in that values of electrical stimulating signal parameters are selectively varied according to data collected by at least one of sensing units including an inertial measurement unit, a voice recording unit or an image capturing unit.

18. An electro-stimulation device (100) as set forth in claim 17, characterized in that the inertial measurement unit with an accelerometer in signal communication with the control unit is provided to collect movement data from a human body.

19. An electro-stimulation device (100) as set forth in claim 18, characterized in that the accelerometer is placed in the body of the ear insert (110) and signals coming from head and neck are filtered out.

20. An electro-stimulation device (100) as set forth in claim 8, characterized in that a voice recording unit in signal communication with the control unit is provided to monitor voice parameters including intensity, speed and swallowing duration of a patient.

21. An electro-stimulation device (100) as set forth in claim 20, characterized in that voice parameters including intensity, speed and swallowing duration are analyzed real-time or as a pre-recorded sample.

22. An electro-stimulation device (100) as set forth in claim 8, characterized in that an image capturing unit in signal communication with the control unit is provided to capture images from different body portions or extremities of a patient to detect symptoms such as tremors.

23. An electro-stimulation device (100) as set forth in claim 1, characterized in that an acoustic channel (130) is open through the length of the ear insert to allow sound from the outside to reach the tympanic membrane.

24. An electro stimulation device (100) as set forth in claim 1, characterized in that the ear insert comprises an amplifier tip amplify sound from the outside as it reaches the tympanic membrane.

25. An electro-stimulation device (100) as set forth in claim 1, characterized in that the signal produced by the control unit has a voltage of 0V-15V and the frequency thereof is between 2 Hz-250 Hz.

26. An electro-stimulation device (100) as set forth in claim 1, characterized in that two electro-stimulation devices (100) are operable in a simultaneous manner in the manner that the electrical stimulating signal generated during a stimulating state is applied by said two electro-stimulation devices at both ears in a synchronized manner.

27. An electro-stimulation device (100) as set forth in claim 1, characterized in that electro-stimulation device (100) comprises a temperature sensor such that temperature of the stimulation end is continuously monitored to avoid excessive heating thereof beyond a predetermined limit.

28. An electro-stimulation device (100) as set forth in claim 27, characterized in that electro-stimulation device (100) is operated such that the stimulation end's initial temperature and temperature thereof at the end of a predetermined inactive period prior to the stimulation are monitored and the active state temperature of the stimulation end is intermittently decreased to the temperature of a respective external ear canal region as measured at the end of the predetermined inactive period of the stimulation end.

29. An electro-stimulation device (100) as set forth in claim 1, characterized in that the stimulating signal includes signal components in the bursting frequencies.

30. An electro-stimulation device (100) as set forth in claim 8, characterized in that the intensity, speed and swallowing duration values are analyzed by a speech processing software.

31. An electro-stimulation device (100) as set forth in claim 1, characterized in that said electro-stimulation device (100) comprises at least one electrode (120) placed on the surface of the ear insert (110) with the stimulation end thereof being adapted to generate an electrical, stimulating signal during a stimulating state in the manner that the position of at least one electrode (120) is adapted to transcutaneously stimulate sympathetic nerves innervating posterior auricular artery, superficial temporal artery or deep auricular artery of the external ear canal (10).

\* \* \* \* \*